(12) United States Patent
Christians

(10) Patent No.: US 8,389,676 B2
(45) Date of Patent: Mar. 5, 2013

(54) BIOTINYLATION TAG PEPTIDES

(75) Inventor: Fred Christians, Los Altos Hills, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 173 days.

(21) Appl. No.: 12/815,160

(22) Filed: Jun. 14, 2010

(65) Prior Publication Data

US 2011/0306096 A1    Dec. 15, 2011

(51) Int. Cl.
*A61K 38/00* (2006.01)
*C12P 21/06* (2006.01)
*C12N 15/00* (2006.01)

(52) U.S. Cl. .............. 530/300; 435/69.1; 435/320.1

(58) Field of Classification Search .......... None
See application file for complete search history.

(56) References Cited

U.S. PATENT DOCUMENTS

| | | |
|---|---|---|
| 5,723,584 A | 3/1998 | Schatz |
| 5,874,239 A | 2/1999 | Schatz |
| 5,932,433 A | 8/1999 | Schatz |
| 6,265,552 B1 | 7/2001 | Schatz |

OTHER PUBLICATIONS

Dosenovic et al., Selective expansion of HIV-1 envelope glycoprotein-specific B cell subsets recognizing distinct structural elements following immunization. The Journal of Immunology., (Sep. 1, 2009), vol. 183(5), pp. 3373-3382.*

* cited by examiner

*Primary Examiner* — Alexander Kim
(74) *Attorney, Agent, or Firm* — Quine Intellectual Property Law Group, P.C.; Monicia Elrod-Erickson; Robert Reamy

(57) ABSTRACT

Biotinylation peptides are provided which can be fused with other peptides or proteins of interest using recombinant DNA techniques to provide efficient methods for biotinylating the resulting fusion proteins in vivo or in vitro.

12 Claims, No Drawings

BIOTINYLATION TAG PEPTIDES

CROSS-REFERENCE TO RELATED APPLICATIONS

Not applicable.

STATEMENT REGARDING FEDERALLY SPONSORED RESEARCH

Not Applicable.

INCORPORATION-BY-REFERENCE OF MATERIAL SUBMITTED BY U.S.P.T.O. EFS-WEB

The instant application contains a Sequence Listing which is being submitted in computer readable form via the United States Patent and Trademark Office eFS-WEB system and which is hereby incorporated by reference in its entirety for all purposes. The txt file submitted herewith contains only one 11 KB file (105-011400US_replacement_ST25.txt).

FIELD OF THE INVENTION

The present invention relates to methods for producing biotinylated proteins in vitro and in recombinant host cells. The invention therefore relates to the field of molecular biology, but given the diverse uses for recombinant proteins, the invention also relates to the fields of chemistry, pharmacology, biotechnology, and medical diagnostics.

DESCRIPTION OF THE BACKGROUND ART

The ability to synthesize DNA chemically has made possible the construction of peptides and proteins not otherwise found in nature and useful in a wide variety of methods that would otherwise be very difficult or impossible to perform. One illustrative example of this technology relates to the class of molecules known as receptors. Receptor proteins mediate important biological functions through interactions with ligands. For many years, researchers have attempted to isolate and identify ligands that interact with receptors in ways that can help ameliorate human (and other) disease. The advent of molecular biology has revolutionized the way these researchers study receptor-ligand interaction. For instance, standard molecular biology techniques have enabled the cloning and high-level expression of many receptors in recombinant host cells.

The patent literature, for instance, is replete with publications describing the recombinant expression of receptor proteins. See, e.g., PCT patent Pub. No. 91/18982 and U.S. Pat. Nos. 5,081,228 and 4,968,607, which describe recombinant DNA molecules encoding the IL-1 receptor; U.S. Pat. Nos. 4,816,565; 4,578,335; and 4,845,198, which describe recombinant DNA and proteins relating to the IL-2 receptor; PCT patent Pub. No. 91/08214, which describes EGF receptor gene related nucleic acids; PCT patent Pub. No. 91/16431 and U.S. Pat. No. 4,897,264, which describe the interferon gamma receptor and related proteins and nucleic acids; European Patent Office (EPO) describes the EPO receptor and related nucleic acids; and PCT patent Pub. No. 92/01715, which describes MHC receptors.

Several of the above publications not only describe how to isolate a particular receptor protein (or the gene encoding the protein) but also describe variants of the receptor that may be useful in ways the natural or native receptor is not. For instance, PCT patent Pub. No. 91/16431 describes soluble versions of the gamma interferon receptor, while PCT patent Pub. No. 92/01715 describes how to produce soluble cell-surface dimeric proteins. This later technology involves expression of the receptor with a signal for lipid attachment; once the lipid is attached to the receptor, the receptor becomes anchored in the cell membrane, where the dimeric form of the receptor is assembled. See also U.S. patent application Ser. No. 947,339, filed on Sep. 18, 1992, and incorporated herein by reference for all purposes, which describes how HPAP-containing receptors can be cleaved from the cell surface and how the anchoring sequences that remain can serve as recognition sequences for antibodies that are used to immobilize the receptor.

The advances made with respect to receptor cloning and expression have been accompanied by advances in technology relating to methods for screening a receptor against compounds that may interact with the receptor in a desired fashion. One such advance relates to the generation of large numbers of compounds, or potential ligands, in a variety of random and semi-random "peptide diversity" generation systems. These systems include the "peptides on plasmids" system described in U.S. Pat. No. 5,338,665, which is a continuation-in-part of U.S. Pat. No. 5,270,170; the "peptides on phage" system described in U.S. patent application Ser. No. 718,577, filed Jun. 20, 1991, which is a continuation-in-part of Ser. No. 541,108, filed Jun. 20, 1990; Cwirla et al., August 1990, Proc. Natl. Acad. Sci. USA 87: 6378-6382; Barrett et al., 1992, Analyt. Biochem. 204: 357-364; and PCT patent Pub. Nos. 91/18980 and 91/19818; the phage-based antibody display systems described in U.S. patent application Ser. No. 517,659, filed May 11, 1990, and PCT patent Pub. No. 91/17271; the bead-based systems for generating and screening nucleic acid ligands described in PCT Pub. Nos. 91/19813, 92/05258, and 92/14843; the bead-based system described in U.S. patent application Ser. No. 946,239, filed Sep. 16, 1992, which is a continuation-in-part of Ser. No. 762,522, filed Sep. 18, 1991; and the "very large scaled immobilized polymer synthesis" system described in U.S. Pat. No. 5,143,854; PCT patent Pub. Nos. 90/15070 and 92/10092, U.S. patent application Ser. No. 624,120, filed Dec. 6, 1990; Fodor et al., Feb. 15, 1991, Science 251: 767-773; Dower and Fodor, 1991, Ann. Rep. Med. Chem. 26:271-180; and U.S. patent application Ser. No. 805,727, filed Dec. 6, 1991. Each of the above references is incorporated herein by reference for all purposes.

Other developments relate to how the receptor is used in such screening methods. One important advance relates to the development of reagents and methods for immobilizing one or more receptors in a spatially defined array, as described in PCT patent Pub. No. 91/07087. In one embodiment of this method, a receptor is attached to avidin and then immobilized on a surface that bears biotin groups. The surface is first prepared, however, with caged biotin groups, which will not bind avidin until the caging group is removed by, in this embodiment, irradiation. Once the avidinylated receptor is bound to the biotin groups on the surface, the surface can be used in screening compounds against the receptor.

Biotin is a coenzyme that is covalently attached to several enzymes involved in the transfer of activated carboxyl groups. As the above example illustrates, biotin labeling of molecules not normally biotinylated can be used to label, detect, purify, and/or immobilize such molecules. These methods also rely upon the proteins avidin and streptavidin, which bind very tightly and specifically to biotin and other biotin-binding molecules, some of which bind to biotin with different affinity than avidin. Typically, the biotinylated molecules used in such methods are prepared by an in vitro biotinylation process. A method for biotinylating proteins synthesized by recombinant DNA techniques in vivo would eliminate the need to biotinylate these proteins chemically after purification and would greatly simplify the purification process, due to the ability to use the biotin as an affinity tag (see Green, 1975, Adv. Protein Res. 29:85-133, incorporated herein by reference).

Biotin is added to proteins in vivo through the formation of an amide bond between the biotin carboxyl group and the epsilon-amino group of specific lysine residues in a reaction that requires ATP. In normal *E. coli*, only one protein is biotinylated, the biotin carboxyl carrier protein (BCCP) subunit of acetyl-CoA carboxylase. This reaction is catalyzed by the biotin-protein ligase (BirA), the product of the birA gene (see Cronan, 1989, Cell 58: 427-429, incorporated herein by reference).

Others have proposed a means by which biown labeling can be accomplished in vivo by the addition of a domain of at least 75 amino acids to recombinant proteins (see Cronan, 1990, J. Biol. Chem. 265: 10327-10333, incorporated herein by reference). See also Cress et al., 1993, Promega Notes 42: 2-7. Addition of this 75 amino acid domain to several different proteins leads to the biotinylation of the fusion proteins by BirA on a specific lysine of the added domain. Addition of smaller fragments of the 75 residue domain does not lead to biotinylation, implying that a reasonably complex recognition domain is required. Changes in the sequence of biotinylated proteins as far as 33 residues from the modified lysine abolish biotinylation (see Murtif and Samols, 1987, J. Biol. Chem. 262: 11813-11816). Changes close to the lysine also affect biotinylation (see Shenoy et al., 1988, FASEB J. 2: 2505-2511, and Shenoy et al., 1992, J. Biol. Chem. 267: 18407-18412); Unfortunately, however, the addition of such a large protein domain may negatively affect the biochemical properties of a biolinylated protein. Smaller domains that specify biotinylation would be very beneficial, in that such domains would have a minimal structural effect on the wide variety of possible fusion partners. Also, the 75 residue domain does not lead to complete biotinylation of the domain, and improved domains could be more efficient. The present invention provides such improved biotinylation domains.

SUMMARY OF THE INVENTION

The present invention provides useful compounds, reagents, methods, and kits for biotinylating proteins. The invention provides methods for biotinylating a protein by: (a) constructing a recombinant DNA expression vector that encodes a fusion protein comprising said protein and a biotinylation peptide less than about 50 amino acids in length wherein the biotinylation peptide comprises specific sequences provided herein; (b) transforming a recombinant host cell capable of synthesizing a biotinylation enzyme with said vector; and (c) culturing said host cell under conditions in which biotin is present and such that said fusion protein and biotinylation enzyme are expressed, resulting in biotinylation of said fusion protein. If the host cell does not naturally produce biotin, then one can add biotin to the media. In a preferred embodiment, the host cell is *E. coli*, and the biotinylation enzyme is BirA.

Thus, a biotinylation peptide of the present invention can be added to any protein expressed in *E. coli* with a sufficient time of retention in the cytoplasm to permit BirA to act. If high expression levels of biotinylated protein are desired, then one can readily overexpress the BirA protein at the same time (see Buoncristiani et al., 1988, J. Biol. Chem. 263, 1013-1016, incorporated herein by reference). In similar fashion, host cells that lack an endogenous biotin protein ligase (called a biotinylation enzyme) can be transformed with a vector that codes for expression of the birA gene to provide or enhance their ability to biotinylate recombinant proteins. Where, due to the conservation of the recognition domains, the endogenous biotin-protein ligase of other non-*E. coli* cell types recognize the novel biotinylation sequences, no such recombinant expression of a biotinylation enzyme is required. One can also perform the biotinylation reaction in vitro using a biotinylation enzyme such as purified BirA (see Buoncristiani, supra), biotin, and biotinylation sequence peptide-tagged proteins, which proteins may be either produced in recombinant host cells or by in vitro translation. One can also use biotin analogues, such as 2-iminobiotin, which has a lower affinity for avidin than biotin and so may be preferred for some applications, in place of biotin, in like method.

The present invention also provides reagents useful in the present method, including peptides, proteins, oligonucleotides, and recombinant DNA expression vectors. Thus, the present invention provides biotinylated peptides less than 50 amino acids in length, typically 10 to 20 or more amino acids in length, and oligonucleotides comprising coding sequences for such peptides. In addition, the invention provides recombinant biotinylated proteins and expression vectors encoding those proteins. In a preferred embodiment the present biotinylation peptide is 13 amino acids long and is defined by Xaa.sub.0 Xaa.sub.1 Xaa.sub.2 Xaa.sub.2.5, Xaa.sub.3 Xaa.sub.4 Xaa.sub.5 Xaa.sub.6 Lys Xaa.sub.7 Xaa.sub.8 Xaa.sub.9 Xaa.sub.10 (SEQ ID NO:1), where Xaa.sub.0 is Leu or Ile; Xaa.sub.1 is any amino acid; Xaa.sub.2 is any amino acid other than Val, Ile, Trp, Phe, or Tyr; Xaa.sub.2.5 is Leu, Ile, or Phe Xaa.sub.3 is Phe or Leu, or Val; Xaa.sub.4 is Glu, Asp, His, Asn, or Ser; Xaa.sub.5 is Ala, Gly, Ser, or Thr; Xaa.sub.6 is Gln or Met; Xaa.sub.7 is Ile, Met, or Val; Xaa.sub.8 is Glu, Leu, Val, Tyr, or Ile; Xaa.sub.9 is Trp, Tyr, Val, Phe, Leu, or Ile; and Xaa.sub.10 is any amino add other than Asp or Glu, wherein either Xaa.sub.0 is I, or Xaa.sub.2 is Leu, or Xaa.sub.2.5 is either Leu or Phe, or Xaa.sub.3 is Val, or Xaa.sub.4 is either His, Asn, or Ser.

In summary, this invention provides a simple and efficient means to biotinylate recombinant proteins, providing for rapid purification, mobilization, labeling, and detection of those proteins. The method is useful for a variety of purposes and is widely commercially useful for research and diagnostic applications,

DESCRIPTION OF THE PREFERRED EMBODIMENT

I. Definitions

For purposes of understanding the present invention, the following terms are defined.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

The term "antibody" refers to antibodies and antibody fragments that retain the ability to bind the epitope that the intact antibody binds, whether the antibody or fragment is produced by hybridoma cell lines, by immunization to elicit a polyclonal antibody response, or by recombinant host cells that have been transformed with a recombinant DNA expression vector that encodes the antibody or antibody fragment.

The term "antigen" is defined as a molecule that induces the formation of an antibody or is capable of binding specifically to the antigen-binding sites of an antibody.

The term "biotinylation peptide" refers to an amino acid sequence which provides a biotinylatable sequence motif. Thus, a biotinylation peptide is peptide that is capable of being biotinylated.

The term "biotinylation enzyme" refers to the class of enzymes known as biotin protein ligases, or enzymes which biotinylate other proteins or peptides.

The term "effective amount" refers to an amount sufficient to induce a desired result The term "epitope" refers to that portion of an antigen that interacts with an antibody.

The term "fusion protein" generally refers to a protein which is a composite of two separate proteins which are normally not fused together as a single protein. Fusion proteins may be prepared by recombinant nucleic acid methods, i.e., as a result of transcription and translation of a gene fusion comprising a segment which encodes a biotinylation peptide and a segment which encodes one or more heterologous proteins, or by chemical synthesis methods well known in the art.

The term "host cell" refers to a eukaryotic or procaryotic cell or group of cells that can be or has been transformed by a recombinant DNA vector. For purposes of the present invention, procaryotic host cells are preferred.

The term "ligand" refers to a molecule that is recognized by a particular receptor. The agent bound by or reacting with a receptor is called a "ligand," a term which is definitionally meaningful primarily in terms of its counterpart receptor. The term "ligand" does not imply any particular molecular size or other structural or compositional feature other than that the substance in question is capable of binding or otherwise interacting with the receptor. A "ligand" may serve either as the natural ligand to which the receptor binds or as a functional analogue that may act as an agonist or antagonist. Examples of ligands that can be investigated with the present invention include, but are not restricted to, peptides and proteins such as agonists and antagonists for cell membrane receptors, toxins and venoms, epitopes such as viral epitopes, antibodies, hormones, enzyme substrates, and proteins.

The term "linker" or "spacer" refers to a molecule or group of molecules (such as a monomer or polymer) that connects two molecules and often serves to place the two molecules in a preferred configuration, e.g., so that a ligand can bind to a receptor with minimal steric hindrance.

The term "monomer" refers to any member of the set of molecules that can be joined together to form an oligomer or polymer. The set of monomers useful in the present invention includes, but is not restricted to, for the example of peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either sub unit alone.

The term "oligomer" or "polymer" refers to the compounds formed by the chemical or enzymatic addition of two or more monomers to one another. Such oligomers include, for example, both linear, cyclic, and branched polymers of nucleic acids and peptides, which peptides can have either alpha-, beta-, or omega-amino acids.

The term "oligonucleotide" refers to a single-stranded DNA or RNA molecule or to analogs of either. Suitable oligonucleotides may be prepared by the phosphoramidite method described by Beaucage et al., 1981, Tetr. Lett. 22:1859-1862, or by the triester method, according to Matteucci et al., 1981, J. Am. Chem. Soc. 103:3185, or by other methods, such as by using commercially available, automated oligonucleotide synthesizers.

The term "operably linked" refers to the placement of one nucleic acid into a functional relationship with another nucleic acid. For instance, a promoter is "operably linked" to a coding sequence if the promoter causes the transcription of the coding sequence. Generally, "operably linked" means that the DNA sequences being linked are contiguous and, where necessary to join two peptide or protein coding regions, in reading frame with one another.

The term "peptide" refers to an oligomer in which the monomers are amino acids (usually alpha-amino acids) joined together through amide bonds. Alternatively, a "peptide" can be referred to as a "polypeptide." Peptides are more than two amino acid monomers long, but more often are more than 5 to 10 amino acid monomers long and can be even longer than 20 amino acids, although peptides longer than 20 amino acids are more likely to be called "polypeptides."

The term "protein" is well known in the art and usually refers to a very large polypeptide, or set of associated polypeptides, that has some biological function. For purposes of the present invention the terms "peptide," "polypeptide," and "protein" are largely interchangeable as libraries of all three types can be prepared using substantially similar methodology.

The term "random peptide" refers to an oligomer composed of two or more amino acid monomers and constructed by a means with which one does not entirely preselect the specific sequence of any particular oligomer. The term "random peptide library" refers not only to a set of recombinant DNA vectors that encodes a set of random peptides, but also to the set of random peptides encoded by those vectors, as well as the fusion proteins containing those random peptides. The term "protein library" has a meaning similar to "random peptide library," but the different library members differ with respect to the amino acid sequence of, or coding sequence for, the protein of interest, so that the library serves as a collection of related but different versions of the same protein.

The term "receptor" refers to a molecule that has an affinity for a given ligand. Receptors may be naturally-occurring or synthetic molecules. Receptors can be employed in their unaltered natural or isolated state, in a recombinant or modified form, or as aggregates with other species: Examples of receptors that can be employed in the method of the present invention include, but are not restricted to, antibodies, cell membrane receptors, monoclonal antibodies, antisera reactive with specific antigenic determinants (such as on viruses, cells, or other materials), polynucleotides, nucleic acids, lectins, polysaccharides, cells, cellular membranes, viruses, and organelles. Receptors are sometimes referred to in the art as "anti-ligands." As the term "receptor" is used herein, no difference in meaning is intended. A "ligand-receptor pair" is formed when a receptor and ligand have combined through molecular recognition to form a complex.

The terms "recombinant DNA cloning vector" and "recombinant DNA expression vector" refer to a DNA or RNA molecule that encodes a useful function and can either be used to transform a host cell or be introduced into a cell-free translation system to produce a protein encoded by the vector. For purposes of the present invention, a cloning vector typically serves primarily as an intermediate in the construction of an expression vector; the latter vector is used to transform or transfect a host cell (or is introduced into a cell-free transcription and translation system) so that the transformed host cell (or cell-free transcription and translation system) produces a protein or other product encoded by the vector. Such vectors are typically "plasmids," which, for purposes of the present invention, are vectors that can be extrachromosomally maintained in a host cell, but can also be vectors that integrate into the genome of a host cell. Those of skill in the art may refer to "cloning vectors", as defined herein, as "vectors" and to "expression vectors," as defined herein, as "plasmids."

The term "solid support" refers to a material having a rigid or semi-rigid surface. Such materials will preferably take the form of small beads, pellets, disks, chips, or wafers, although other forms may be used. In some embodiments, at least one surface of the solid support will be substantially flat.

The term "surface" refers to any generally two-dimensional structure on a solid substrate and may have steps, ridges, kinks, terraces, and the like without ceasing to be a surface.

The term "synthetic" refers to production by in vitro chemical or enzymatic synthesis.

II. Methods and Reagents of the Invention

The inventors have designed the set of small, efficient peptide biotinylation sequences of the present invention, and peptides were constructed which incorporated these sequences. It is known in the art that certain short sequences can act as biotinylation sequences. See, for example, U.S. Pat. No. 5,723,584, which describes a specific set of peptide biotinylation sequences.

As discussed above, the short, biotinylation peptides of the invention can be biotinylated in vivo or in vitro and can be used for a wide variety of purposes, including purification, immobilization, labeling, and detection of proteins. A few illustrative examples include: (1) labeling receptors with biotin at a defined site, so that the labeled receptor could be, for instance, bound to streptavidin to produce a tetravalent receptor to increase the sensitivity of binding assays, such as those described in U.S. Pat. No. 5,143,854, and U.S. patent application Ser. No. 946,239, filed Sep. 16, 1992, each of which is incorporated herein by reference; (2) labeling fusion proteins containing peptide leads from any screening program, so that the labeled fusion proteins can be used to test binding of the peptide to receptors in a monovalent format (by probing with labeled streptavidin after binding occurs) or in a multivalent format (by prebinding the fusions to labeled streptavidin and then testing binding to receptors or so that the peptides can be mobilized on streptavidin-coated beads or in microtiter wells for probing with receptors, such as protease enzymes, in solution; (3) labeling peptides or proteins directly by growing cells in the presence of tritiated biotin—with a biotin auxotrophs the peptides could be labeled at a known specific activity to permit quantitative measurements of binding activity; (4) developing technology for doing enzymatic reactions on surfaces by exposing libraries of variant immobilized sequences to BirA, biotin, and ATP, so that those peptides that were substrates would be biotinylated and could be detected with labeled streptavidin; and (5) attaching biotin specifically to an enzyme such as a polymerase enzyme to allow for binding the enzyme to a surface, for example for single molecule sequencing, e.g. as described in U.S. Pat. No. 7,056,661 and U.S. patent application Ser. No. 12/414,191.

This invention also embraces kits which are useful for producing proteins containing biotinylation peptides. Such kits comprise, for instance, a recombinant expression polynucleotide which can be used to produce the peptides of the invention fused to a coding sequence of choice, and directions for using the polynucleotides. DNA expression polynucleotides may be destined to replicate episomally or to integrate into the chromosome of the host cell chosen for expression. Frequently, the DNA polynucleotides of the kit contain a multiple cloning site linked to sequence coding for the peptides of the inventions such that any coding sequence may be inserted in the correct translational reading frame for expression. These kits may be used to produce the peptides of the invention fused to the amino terminus the carboxyl terminus or internal to the coding sequence of choice. Within these fusion proteins, the peptides of the invention may be separated from the coding sequences by additional spacer sequences.

Expression of coding sequence will preferably be under control of an inducible promoter; some examples are the lac or tac promoter in $E.\ coli$, the gal4 promoter in $S.\ cerevisiae$, the glaA promoter in *Aspergillus niger*, or the murine metallothionein promoter in many mammalian cells. Alternatively, constitutive promoters may be desirable for certain applications, such as the SV40 early promoter in mammalian cells. For some applications, such as in vitro translation in rabbit reticulocytes, the ability to synthesize RNA in vitro using a RNA polymerase such as that from the bacteriophage SP6 will be needed. In that case, signals for initiation of transcription by both SP6 RNA polymerase and an alternative RNA polymerase can be operably linked to the same expression sequence.

Besides a promoter for initiation of the expression sequences, the polynucleotides of the kits will also preferably contain sequences for transcriptional termination, such as the T7 terminator in $E.\ coli$ or the SV40 terminator in mammalian cells. Additionally, when the proteins are expressed in mammalian cells, a signal for polyadenylation is desirable, such as the SV40 polyadenylation sequence.

Of course, additional sequences may also be included in the polynucleotides of these kits which will confer additional properties on the proteins produced. For example, a signal sequence which causes the expressed proteins to be secreted from the cell may be incorporated into the polynucleotides. Sequences which serve to link expressed proteins to the membrane, such as a sequence encoding a hydrophobic membrane spanning domain, or an encoded sequence which signals attachment of a glycosylphosphatidylinositol membrane anchor to the protein, may be included as part of the expression polynucleotide. The polynucleotides may also encode a sequence recognized by a protease, such as factor $X_a$, adjacent to the sequence encoding the biotinylation peptides of the invention. One of skill in the art will recognize that these and many other combinations of additional sequences may be advantageous.

Other constituents of the kits may comprise host cells suitable for obtaining expression from the polynucleotide, avidin or streptavidin coupled to a solid support, avidin or streptavidin coupled to a detectable label such as the enzyme horseradish peroxidase, a biotinylation enzyme such as purified BirA, and instructions for analysis and purification of the proteins expressed using these kits. Preferably, the host cells will express a biotinylating enzyme. Optionally, polynucleotides which, when transformed into host cells, cause the production or overproduction of biotinylating enzymes may be supplied in the kits, or the host cells provided with the kits may be already modified to produce or over-produce biotinylating enzymes. However, for some applications the absence of biotinylating enzyme in the host cell may be advantageous. For example, the kit user may prefer to biotinylate the expressed fusion proteins in vitro.

III. Examples

Each of the DNA sequences encoding the affinity peptides was added individually to the 5' terminus of a His(10)-tagged phi29 DNA polymerase gene such that the polypeptide expressed from each construct was a fusion protein consisting of: N-terminus-biotinylation peptide-His(10)-phi29 pol-C-terminus. Each gene was expressed in E. coli cells co-expressing biotin ligase in culture medium containing biotin. These conditions are known to effect the in-vivo biotinylation of biotinylation peptides. Proteins were purified using Ni-NTA columns and then mixed with a 2-fold molar excess of streptavidin under conditions known to effect binding of streptavidin to biotinylated fusion proteins.

The degree of biotinylation of each protein was assessed by HPLC. Of the proteins tested (SEQ ID NO:2-12) all were found to be essentially 100% bound to streptavidin under these conditions except SEQ ID NO:2 (Leu Asn Asp Leu Phe His Ala Gln Lys Ile Glu Trp His) and SEQ ID NO:9 (Leu Asn Asp Ile Val Glu Ala Gln Lys Ile Glu Trp His), which were approximately 50% bound. None of the biotinylation peptides affected the polymerase activity when tested in a branching fraction assay performed, for example, as described in U.S. patent application No. 2010/0112645.

Those of skill in the art recognize from the description above that the present invention provides many advantages and more application than prior art methods for biotinylating proteins. The biotinylation peptides of the invention are small but specific, allowing one to label a protein at a defined site, at either end of or internally to the protein to be labeled. The invention provides an improved immobilization method, allowing one to avoid the use of antibodies and the problems attendant thereto. The high binding affinity of the avidin-biotin interaction provides advantages for labeling, localization, detection, immobilization, and purification methods as well. For instance, one could use the biotinylation peptides of the invention to purify BirA protein or other biotinylation reaction can occur in vivo (where few other proteins are naturally biotinylated) or in vitro, with readily available materials. As can be appreciated from the disclosure above, the present invention has a wide variety of applications. Accordingly, the following examples are offered by way of illustration, not by way of limitation.

What is claimed is:

1. A biotinylation peptide comprising:

a non-naturally occurring peptide sequence of 13 to 50 amino acid residues comprising the amino acid sequence:

Xaa.sub.0 Xaa.sub.1 Xaa.sub.2 Xaa.sub.2.5, Xaa.sub.3 Xaa.sub.4 Xaa.sub.5 Xaa.sub.6 Lys Xaa.sub.7 Xaa.sub.8 Xaa.sub.9 Xaa.sub.10, wherein a) Xaa.sub.0 is Ile;
Xaa.sub.1 is any amino acid;
Xaa.sub.2 is any amino acid other than Val, Ile, Trp, Phe, or Tyr;
Xaa.sub.2.5 is Leu, Ile, or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:13), b) Xaa.sub.0 is Leu or Ile;
Xaa.sub.1 is any amino acid;

Xaa.sub.2 is Leu;
Xaa.sub.2.5 is Leu, Ile, or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:14),
c) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:15),
d) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu, Ile, or Phe;
Xaa.sub.3 is Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:16), or
e) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu, Ile, or Phe;
Xaa.sub.3 is Phe, Leu, or Val;
Xaa.sub.4 is His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:17); and
wherein said biotinylation peptide is capable of being biotinylated by a biotin ligase at the lysine residue adjacent to Xaa.sub.6.

2. The biotinylation peptide of claim 1 wherein said biotinylation sequence has been biotinylated by a biotin ligase.

3. The biotinylation peptide of claim 1 or claim 2, wherein either the carboxyl or amino terminus of said biotinylation peptide is covalently coupled to a protein that is incapable of being biotinylated by a biotin-ligase.

4. The biotinylation peptide of claim 1 or claim 2 wherein the carboxyl terminus of said biotinylation peptide is covalently coupled to a first protein that is incapable of being biotinylated by a biotin ligase, and wherein the amino terminus of said biotinylation peptide is coupled to a second protein that is incapable of being biotinylated by a biotin ligase.

5. The biotinylation peptide of claim 1 or claim 2 wherein said biotin ligase is BirA.

6. The biotinylation peptide of claim 1 wherein the non-naturally occurring peptide sequence of 13 to 50 amino acid residues comprises the sequence:

```
                                          (SEQ ID NO: 2)
Leu Asn Asp Leu Phe His Ala Gln Lys Ile Glu

Trp His,
                                          (SEQ ID NO: 3)
Leu Asn Asp Phe Phe Asn Ala Gln Lys Ile Glu

Trp His,
                                          (SEQ ID NO: 4)
Ile Asn Asp Leu Phe Ser Ala Gln Lys Ile Glu

Trp His,
                                          (SEQ ID NO: 5)
Ile Asn Asp Ile Phe Glu Ala Gln Lys Ile Glu

Trp His,
                                          (SEQ ID NO: 6)
Leu Asn Leu Ile Phe Glu Ala Gln Lys Ile Glu

Trp His,
                                          (SEQ ID NO: 7)
Leu Asn Asp Leu Phe Glu Ala Gln Lys Ile Glu

Trp His,
                                          (SEQ ID NO: 8)
Leu Asn Asp Phe Phe Glu Ala Gln Lys Ile Glu

Trp His,
                                          (SEQ ID NO: 9)
Leu Asn Asp Ile Val Glu Ala Gln Lys Ile Glu

Trp His,
                                          (SEQ ID NO: 10)
Leu Asn Asp Ile Phe His Ala Gln Lys Ile Glu

Trp His,
                                          (SEQ ID NO: 11)
Leu Asn Asp Ile Phe Asn Ala Gln Lys Ile Glu

Trp His,
or
                                          (SEQ ID NO: 12)
Leu Asn Asp Ile Phe Ser Ala Gln Lys Ile Glu

Trp His.
```

7. A method for biotinylating a protein, said method comprising:
(a) constructing a recombinant DNA expression vector that encodes a fusion protein comprising said protein and a biotinylation peptide wherein said biotinylation peptide comprises the amino acid sequence Xaa.sub.0 Xaa.sub.1 Xaa.sub.2 Xaa.sub.2.5, Xaa.sub.3 Xaa.sub.4 Xaa.sub.5 Xaa.sub.6 Lys Xaa.sub.7 Xaa.sub.8 Xaa.sub.9 Xaa.sub.10,
wherein
i) Xaa.sub.0 is Ile;
Xaa.sub.1 is any amino acid;
Xaa.sub.2 is any amino acid other than Val, Ile, Trp, Phe, or Tyr;

Xaa.sub.2.5 is Leu, Ile, or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:13),
ii) Xaa.sub.0 is Leu or Ile;
Xaa.sub.1 is any amino acid;
Xaa.sub.2 is Leu;
Xaa.sub.2.5 is Leu, Ile, or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:14),
iii) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:15),
iv) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu, Ile, or Phe;
Xaa.sub.3 is Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:16), or
v) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu, Ile, or Phe;
Xaa.sub.3 is Phe, Leu, or Val;
Xaa.sub.4 is His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:17); and wherein said biotinylation peptide is capable of being biotinylated by a biotin ligase at said lysine residue adjacent to Xaa.sub.6 and is 13 to 50 amino acids in length;
(b) transforming a recombinant host cell with said vector; and
(c) culturing said host cell in the presence of biotin or a biotin analogue and under conditions such that said fusion protein and a biotinylation enzyme are expressed, resulting in biotinylation of said fusion protein.

8. A method for biotinylating a protein, said method comprising:
(a) constructing a recombinant DNA expression vector that encodes a fusion protein comprising said protein and a biotinylation peptide wherein said biotinylation peptide comprises the amino acid sequence Xaa.sub.0 Xaa.sub.1 Xaa.sub.2 Xaa.sub.2.5, Xaa.sub.3 Xaa.sub.4 Xaa.sub.5 Xaa.sub.6 Lys Xaa.sub.7 Xaa.sub.8 Xaa.sub.9 Xaa.sub.10 (SEQ ID NO:1),
wherein
i) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu, Ile, or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:13),
ii) Xaa.sub.0 is Leu or Ile;
Xaa.sub.1 is any amino acid;
Xaa.sub.2 is Leu;
Xaa.sub.2.5 is Leu, Ile, or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:14),
iii) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:15),
iv) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu, Ile, or Phe;
Xaa.sub.3 is Val;

Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:16), or v) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu, Ile, or Phe;
Xaa.sub.3 is Phe, Leu, or Val;
Xaa.sub.4 is His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:17); and wherein said biotinylation peptide is capable of being biotinylated by a biotin ligase at said lysine residue adjacent to Xaa.sub.6 and is 13 to 50 amino acids in length;

(b) producing said fusion protein encoded by said vector either by transforming a recombinant host cell with said vector and culturing host cells transformed with the vector, or by incubating said vector in a cell-free transcription and translation system; and (c) incubating said fusion protein in a reaction mixture comprising biotin or a biotin analogue and a biotinylation enzyme, resulting in biotinylation of said fusion protein.

9. The method of claim 7 or claim 8 wherein the biotinylation peptide comprises the amino acid sequence:

```
                                          (SEQ ID NO: 2)
Leu Asn Asp Leu Phe His Ala Gln Lys Ile Glu

Trp His, (SEQ ID NO: 3)
Leu Asn Asp Phe Phe Asn Ala Gln Lys Ile Glu

Trp His, (SEQ ID NO: 4)
Ile Asn Asp Leu Phe Ser Ala Gln Lys Ile Glu

Trp His, (SEQ ID NO: 5)
Ile Asn Asp Ile Phe Glu Ala Gln Lys Ile Glu

Trp His, (SEQ ID NO: 6)
Leu Asn Leu Ile Phe Glu Ala Gln Lys Ile Glu

Trp His, (SEQ ID NO: 7)
Leu Asn Asp Leu Phe Glu Ala Gln Lys Ile Glu

Trp His, (SEQ ID NO: 8)
Leu Asn Asp Phe Phe Glu Ala Gln Lys Ile Glu

Trp His,
```

```
                                          (SEQ ID NO: 9)
Leu Asn Asp Ile Val Glu Ala Gln Lys Ile Glu

Trp His, (SEQ ID NO: 10)
Leu Asn Asp Ile Phe His Ala Gln Lys Ile Glu

Trp His, (SEQ ID NO: 11)
Leu Asn Asp Ile Phe Asn Ala Gln Lys Ile Glu

Trp His,
or
                                          (SEQ ID NO: 12)
Leu Asn Asp Ile Phe Ser Ala Gln Lys Ile Glu

Trp His.
```

10. A kit for biotinylating a protein, the kit comprising a recombinant DNA expression polynucleotide that encodes a biotinylation peptide wherein said biotinylation peptide comprises the amino acid sequence Xaa.sub.0 Xaa.sub.1 Xaa.sub.2 Xaa.sub.2.5, Xaa.sub.3 Xaa.sub.4 Xaa.sub.5 Xaa.sub.6 Lys Xaa.sub.7 Xaa.sub.8 Xaa.sub.9 Xaa.sub.10, wherein a) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu, Ile, or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:13), b) Xaa.sub.0 is Leu or Ile;
Xaa.sub.1 is any amino acid;
Xaa.sub.2 is Leu;
Xaa.sub.2.5 is Leu, Ile, or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:14), c) Xaa.sub.0 is Leu or Ile;
Xaa.sub.1 is any amino acid;
Xaa.sub.2 is any amino acid other than Val, Ile, Trp, Phe, or Tyr;
Xaa.sub.2.5 is Leu or Phe;
Xaa.sub.3 is Phe, Leu, or Val;
Xaa.sub.4 is Glu, Asp, His, Asn, or Ser;
Xaa.sub.5 is Ala, Gly, Ser, or Thr;
Xaa.sub.6 is Gln or Met;
Xaa.sub.7 is Ile, Met, or Val;
Xaa.sub.8 is Glu, Leu, Val, Tyr, or Ile;
Xaa.sub.9 is Trp, Tyr, Val, Phe, Leu, or Ile; and
Xaa.sub.10 is any amino acid other than Asp or Glu (SEQ ID NO:15), d) Xaa.sub.0 is Leu or Ile;
   Xaa.sub.1 is any amino acid;
   Xaa.sub.2 is any amino acid other than Val, Ile, Trp, Phe, or Tyr;
   Xaa.sub.2.5 is Leu, Ile, or Phe;
   Xaa.sub.3 is Val;
   Xaa.sub.4 is Glu, Asp, His, Asn, or Ser;
   Xaa.sub.5 is Ala, Gly, Ser, or Thr;
   Xaa.sub.6 is Gln or Met;
   Xaa.sub.7 is Ile, Met, or Val;
   Xaa.sub.8 is Glu, Leu, Val, Tyr, or Ile;
   Xaa.sub.9 is Trp, Tyr, Val, Phe, Leu, or Ile; and
   Xaa.sub.10 is any amino acid other than Asp or Glu (SEQ ID NO:16), or
e) Xaa.sub.0 is Leu or Ile;
   Xaa.sub.1 is any amino acid;
   Xaa.sub.2 is any amino acid other than Val, Ile, Trp, Phe, or Tyr;
   Xaa.sub.2.5 is Leu, Ile, or Phe;
   Xaa.sub.3 is Phe, Leu, or Val;
   Xaa.sub.4 is His, Asn, or Ser;
   Xaa.sub.5 is Ala, Gly, Ser, or Thr;
   Xaa.sub.6 is Gln or Met;
   Xaa.sub.7 is Ile, Met, or Val;
   Xaa.sub.8 is Glu, Leu, Val, Tyr, or Ile;
   Xaa.sub.9 is Trp, Tyr, Val, Phe, Leu, or Ile; and
   Xaa.sub.10 is any amino acid other than Asp or Glu (SEQ ID NO:17); and
wherein said biotinylation peptide is capable of being biotinylated by a biotin ligase at said lysine residue adjacent to Xaa.sub.6 and is 13 to 50 amino acids in length; and wherein said biotinylation protein can be fused in frame with a protein by inserting the coding sequence for the protein.

11. The kit of claim 10 wherein the biotinylation peptide comprises the amino acid sequence:

```
                                         (SEQ ID NO: 2)
Leu Asn Asp Leu Phe His Ala Gln Lys Ile Glu

Trp His, (SEQ ID NO: 3)
Leu Asn Asp Phe Phe Asn Ala Gln Lys Ile Glu

Trp His, (SEQ ID NO: 4)
Ile Asn Asp Leu Phe Ser Ala Gln Lys Ile Glu

Trp His, (SEQ ID NO: 5)
Ile Asn Asp Ile Phe Glu Ala Gln Lys Ile Glu

Trp His, (SEQ ID NO: 6)
Leu Asn Leu Ile Phe Glu Ala Gln Lys Ile Glu

Trp His, (SEQ ID NO: 7)
Leu Asn Asp Leu Phe Glu Ala Gln Lys Ile Glu

Trp His, (SEQ ID NO: 8)
Leu Asn Asp Phe Phe Glu Ala Gln Lys Ile Glu

Trp His, (SEQ ID NO: 9)
Leu Asn Asp Ile Val Glu Ala Gln Lys Ile Glu

Trp His, (SEQ ID NO: 10)
Leu Asn Asp Ile Phe His Ala Gln Lys Ile Glu

Trp His, (SEQ ID NO: 11)
Leu Asn Asp Ile Phe Asn Ala Gln Lys Ile Glu

Trp His,
or (SEQ ID NO: 12)
Leu Asn Asp Ile Phe Ser Ala Gln Lys Ile Glu

Trp His.
```

12. The kit of claim 10 wherein the expression polynucleotide is transformed into a host cell.

* * * * *

SEQUENCE LISTING

```
<160> NUMBER OF SEQ ID NOS: 17

<210> SEQ ID NO 1
<211> LENGTH: 13
<212> TYPE: PRT
<213> ORGANISM: Artificial Sequence
<220> FEATURE:
<223> OTHER INFORMATION: Non-naturally occurring peptide
<220> FEATURE:
<221> NAME/KEY: MISC_FEATURE
<222> LOCATION: (1)..(1)
<223> OTHER INFORMATION: X is Leu or Ile
<220> FEATURE:
<221> NAME/KEY: MISC_FEATURE
<222> LOCATION: (1)..(13)
<223> OTHER INFORMATION: X's at positions 1-8 and 10-13 are chosen from
      the indicated possibilities, as long as either:  X at position 1
      is Ile,  X at position 3 is Leu,  X at position 4 is Leu or Phe,
      X at position 5 is Val, or X at position 6 is His, Asn, or Ser
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is any amino acid other than Val, Ile, Trp,
      Phe, or Tyr
<220> FEATURE:
<221> NAME/KEY: MISC_FEATURE
<222> LOCATION: (4)..(4)
<223> OTHER INFORMATION: X is Leu, Ile, or Phe
<220> FEATURE:
<221> NAME/KEY: MISC_FEATURE
<222> LOCATION: (5)..(5)
<223> OTHER INFORMATION: X is Phe, Leu, or Val
<220> FEATURE:
<221> NAME/KEY: MISC_FEATURE
<222> LOCATION: (6)..(6)
<223> OTHER INFORMATION: X is Glu, Asp, His, Asn, or Ser
<220> FEATURE:
<221> NAME/KEY: MISC_FEATURE
<222> LOCATION: (7)..(7)
<223> OTHER INFORMATION: X is Ala, Gly, Ser, or Thr
<220> FEATURE:
<221> NAME/KEY: MISC_FEATURE
```

```
<222> LOCATION: (8)..(8)
<223> OTHER INFORMATION: X is Gln or Met
<220> FEATURE:
<221> NAME/KEY: MISC_FEATURE
<222> LOCATION: (10)..(10)
<223> OTHER INFORMATION: X is Ile, Met, or Val
<220> FEATURE:
<221> NAME/KEY: MISC_FEATURE
<222> LOCATION: (11)..(11)
<223> OTHER INFORMATION: X is Glu, Leu, Val, Tyr, or Ile
<220> FEATURE:
<221> NAME/KEY: MISC_FEATURE
<222> LOCATION: (12)..(12)
<223> OTHER INFORMATION: X is Trp, Tyr, Val, Phe, Leu, or Ile
<220> FEATURE:
<221> NAME/KEY: MISC_FEATURE
<222> LOCATION: (13)..(13)
<223> OTHER INFORMATION: X is any amino add other than Asp or Glu

<400> SEQUENCE: 1

Xaa Xaa Xaa Xaa Xaa Xaa Xaa Xaa Lys Xaa Xaa Xaa Xaa
 1               5                   10

<210> SEQ ID NO 2
<211> LENGTH: 13
<212> TYPE: PRT
<213> ORGANISM: Artificial Sequence
<220> FEATURE:
<223> OTHER INFORMATION: Non-naturally occurring peptide

<400> SEQUENCE: 2

Leu Asn Asp Leu Phe His Ala Gln Lys Ile Glu Trp His
 1               5                   10

<210> SEQ ID NO 3
<211> LENGTH: 13
<212> TYPE: PRT
<213> ORGANISM: Artificial Sequence
<220> FEATURE:
<223> OTHER INFORMATION: Non-naturally occurring peptide

<400> SEQUENCE: 3

Leu Asn Asp Phe Phe Asn Ala Gln Lys Ile Glu Trp His
 1               5                   10

<210> SEQ ID NO 4
<211> LENGTH: 13
<212> TYPE: PRT
<213> ORGANISM: Artificial Sequence
<220> FEATURE:
<223> OTHER INFORMATION: Non-naturally occurring peptide

<400> SEQUENCE: 4

Ile Asn Asp Leu Phe Ser Ala Gln Lys Ile Glu Trp His
 1               5                   10

<210> SEQ ID NO 5
<211> LENGTH: 13
<212> TYPE: PRT
<213> ORGANISM: Artificial Sequence
<220> FEATURE:
<223> OTHER INFORMATION: Non-naturally occurring peptide

<400> SEQUENCE: 5

Ile Asn Asp Ile Phe Glu Ala Gln Lys Ile Glu Trp His
 1               5                   10

<210> SEQ ID NO 6
<211> LENGTH: 13
<212> TYPE: PRT
```

```
<213> ORGANISM: Artificial Sequence
<220> FEATURE:
<223> OTHER INFORMATION: Non-naturally occurring peptide

<400> SEQUENCE: 6

Leu Asn Leu Ile Phe Glu Ala Gln Lys Ile Glu Trp His
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Non-naturally occurring peptide

<400> SEQUENCE: 7

Leu Asn Asp Leu Phe Glu Ala Gln Lys Ile Glu Trp His
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Non-naturally occurring peptide

<400> SEQUENCE: 8

Leu Asn Asp Phe Phe Glu Ala Gln Lys Ile Glu Trp His
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Non-naturally occurring peptide

<400> SEQUENCE: 9

Leu Asn Asp Ile Val Glu Ala Gln Lys Ile Glu Trp His
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Non-naturally occurring peptide

<400> SEQUENCE: 10

Leu Asn Asp Ile Phe His Ala Gln Lys Ile Glu Trp His
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Non-naturally occurring peptide

<400> SEQUENCE: 11

Leu Asn Asp Ile Phe Asn Ala Gln Lys Ile Glu Trp His
1               5                   10

<210> SEQ ID NO 12
<211> LENGTH: 13
<212> TYPE: PRT
<213> ORGANISM: Artificial Sequence
<220> FEATURE:
```

-continued

<223> OTHER INFORMATION: Non-naturally occurring peptide

<400> SEQUENCE: 12

Leu Asn Asp Ile Phe Ser Ala Gln Lys Ile Glu Trp His
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Non-naturally occurring peptide
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is any amino acid other than Val, Ile, Trp,
      Phe, or Tyr
<220> FEATURE:
<221> NAME/KEY: MISC_FEATURE
<222> LOCATION: (4)..(4)
<223> OTHER INFORMATION: X is Leu, Ile, or Phe
<220> FEATURE:
<221> NAME/KEY: MISC_FEATURE
<222> LOCATION: (5)..(5)
<223> OTHER INFORMATION: X is Phe, Leu, or Val
<220> FEATURE:
<221> NAME/KEY: MISC_FEATURE
<222> LOCATION: (6)..(6)
<223> OTHER INFORMATION: X is Glu, Asp, His, Asn, or Ser
<220> FEATURE:
<221> NAME/KEY: MISC_FEATURE
<222> LOCATION: (7)..(7)
<223> OTHER INFORMATION: X is Ala, Gly, Ser, or Thr
<220> FEATURE:
<221> NAME/KEY: MISC_FEATURE
<222> LOCATION: (8)..(8)
<223> OTHER INFORMATION: X is Gln or Met
<220> FEATURE:
<221> NAME/KEY: MISC_FEATURE
<222> LOCATION: (10)..(10)
<223> OTHER INFORMATION: X is Ile, Met, or Val
<220> FEATURE:
<221> NAME/KEY: MISC_FEATURE
<222> LOCATION: (11)..(11)
<223> OTHER INFORMATION: X is Glu, Leu, Val, Tyr, or Ile
<220> FEATURE:
<221> NAME/KEY: MISC_FEATURE
<222> LOCATION: (12)..(12)
<223> OTHER INFORMATION: X is Trp, Tyr, Val, Phe, Leu, or Ile
<220> FEATURE:
<221> NAME/KEY: MISC_FEATURE
<222> LOCATION: (13)..(13)
<223> OTHER INFORMATION: X is any amino acid other than Asp or Glu

<400> SEQUENCE: 13

Ile Xaa Xaa Xaa Xaa Xaa Xaa Xaa Lys Xaa Xaa Xaa Xaa
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Non-naturally occurring peptide
<220> FEATURE:
<221> NAME/KEY: MISC_FEATURE
<222> LOCATION: (1)..(1)
<223> OTHER INFORMATION: X is Leu or Ile
<220> FEATURE:
<221> NAME/KEY: MISC_FEATURE
<222> LOCATION: (2)..(2)
<223> OTHER INFORMATION: X is any amino acid

```
<220> FEATURE:
<221> NAME/KEY: MISC_FEATURE
<222> LOCATION: (4)..(4)
<223> OTHER INFORMATION: X is Leu, Ile, or Phe
<220> FEATURE:
<221> NAME/KEY: MISC_FEATURE
<222> LOCATION: (5)..(5)
<223> OTHER INFORMATION: X is Phe, Leu, or Val
<220> FEATURE:
<221> NAME/KEY: MISC_FEATURE
<222> LOCATION: (6)..(6)
<223> OTHER INFORMATION: X is Glu, Asp, His, Asn, or Ser
<220> FEATURE:
<221> NAME/KEY: MISC_FEATURE
<222> LOCATION: (7)..(7)
<223> OTHER INFORMATION: X is Ala, Gly, Ser, or Thr
<220> FEATURE:
<221> NAME/KEY: MISC_FEATURE
<222> LOCATION: (8)..(8)
<223> OTHER INFORMATION: X is Gln or Met
<220> FEATURE:
<221> NAME/KEY: MISC_FEATURE
<222> LOCATION: (10)..(10)
<223> OTHER INFORMATION: X is Ile, Met, or Val
<220> FEATURE:
<221> NAME/KEY: MISC_FEATURE
<222> LOCATION: (11)..(11)
<223> OTHER INFORMATION: X is Glu, Leu, Val, Tyr, or Ile
<220> FEATURE:
<221> NAME/KEY: MISC_FEATURE
<222> LOCATION: (12)..(12)
<223> OTHER INFORMATION: X is Trp, Tyr, Val, Phe, Leu, or Ile
<220> FEATURE:
<221> NAME/KEY: MISC_FEATURE
<222> LOCATION: (13)..(13)
<223> OTHER INFORMATION: X is any amino acid other than Asp or Glu

<400> SEQUENCE: 14

Xaa Xaa Leu Xaa Xaa Xaa Xaa Xaa Lys Xaa Xaa Xaa Xaa
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Non-naturally occurring peptide
<220> FEATURE:
<221> NAME/KEY: MISC_FEATURE
<222> LOCATION: (1)..(1)
<223> OTHER INFORMATION: X is Leu or Ile
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is any amino acid other than Val, Ile, Trp,
     Phe, or Tyr
<220> FEATURE:
<221> NAME/KEY: MISC_FEATURE
<222> LOCATION: (4)..(4)
<223> OTHER INFORMATION: X is Leu or Phe
<220> FEATURE:
<221> NAME/KEY: MISC_FEATURE
<222> LOCATION: (5)..(5)
<223> OTHER INFORMATION: X is Phe, Leu, or Val
<220> FEATURE:
<221> NAME/KEY: MISC_FEATURE
<222> LOCATION: (6)..(6)
<223> OTHER INFORMATION: X is Glu, Asp, His, Asn, or Ser
<220> FEATURE:
<221> NAME/KEY: MISC_FEATURE
<222> LOCATION: (7)..(7)
<223> OTHER INFORMATION: X is Ala, Gly, Ser, or Thr
<220> FEATURE:
<221> NAME/KEY: MISC_FEATURE
```

```
<222> LOCATION: (8)..(8)
<223> OTHER INFORMATION: X is Gln or Met
<220> FEATURE:
<221> NAME/KEY: MISC_FEATURE
<222> LOCATION: (10)..(10)
<223> OTHER INFORMATION: X is Ile, Met, or Val
<220> FEATURE:
<221> NAME/KEY: MISC_FEATURE
<222> LOCATION: (11)..(11)
<223> OTHER INFORMATION: X is Glu, Leu, Val, Tyr, or Ile
<220> FEATURE:
<221> NAME/KEY: MISC_FEATURE
<222> LOCATION: (12)..(12)
<223> OTHER INFORMATION: X is Trp, Tyr, Val, Phe, Leu, or Ile
<220> FEATURE:
<221> NAME/KEY: MISC_FEATURE
<222> LOCATION: (13)..(13)
<223> OTHER INFORMATION: X is any amino acid other than Asp or Glu

<400> SEQUENCE: 15

Xaa Xaa Xaa Xaa Xaa Xaa Xaa Xaa Lys Xaa Xaa Xaa Xaa
 1               5                  10

<210> SEQ ID NO 16
<211> LENGTH: 13
<212> TYPE: PRT
<213> ORGANISM: Artificial Sequence
<220> FEATURE:
<223> OTHER INFORMATION: Non-naturally occurring peptide
<220> FEATURE:
<221> NAME/KEY: MISC_FEATURE
<222> LOCATION: (1)..(1)
<223> OTHER INFORMATION: X is Leu or Ile
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is any amino acid other than Val, Ile, Trp,
      Phe, or Tyr
<220> FEATURE:
<221> NAME/KEY: MISC_FEATURE
<222> LOCATION: (4)..(4)
<223> OTHER INFORMATION: X is Leu, Ile, or Phe
<220> FEATURE:
<221> NAME/KEY: MISC_FEATURE
<222> LOCATION: (6)..(6)
<223> OTHER INFORMATION: X is Glu, Asp, His, Asn, or Ser
<220> FEATURE:
<221> NAME/KEY: MISC_FEATURE
<222> LOCATION: (7)..(7)
<223> OTHER INFORMATION: X is Ala, Gly, Ser, or Thr
<220> FEATURE:
<221> NAME/KEY: MISC_FEATURE
<222> LOCATION: (8)..(8)
<223> OTHER INFORMATION: X is Gln or Met
<220> FEATURE:
<221> NAME/KEY: MISC_FEATURE
<222> LOCATION: (10)..(10)
<223> OTHER INFORMATION: X is Ile, Met, or Val
<220> FEATURE:
<221> NAME/KEY: MISC_FEATURE
<222> LOCATION: (11)..(11)
<223> OTHER INFORMATION: X is Glu, Leu, Val, Tyr, or Ile
<220> FEATURE:
<221> NAME/KEY: MISC_FEATURE
<222> LOCATION: (12)..(12)
<223> OTHER INFORMATION: X is Trp, Tyr, Val, Phe, Leu, or Ile
<220> FEATURE:
<221> NAME/KEY: MISC_FEATURE
<222> LOCATION: (13)..(13)
<223> OTHER INFORMATION: X is any amino acid other than Asp or Glu

<400> SEQUENCE: 16

Xaa Xaa Xaa Xaa Val Xaa Xaa Xaa Lys Xaa Xaa Xaa Xaa
```

```
<210> SEQ ID NO 17
<211> LENGTH: 13
<212> TYPE: PRT
<213> ORGANISM: Artificial Sequence
<220> FEATURE:
<223> OTHER INFORMATION: Non-naturally occurring peptide
<220> FEATURE:
<221> NAME/KEY: MISC_FEATURE
<222> LOCATION: (1)..(1)
<223> OTHER INFORMATION: X is Leu or Ile
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is any amino acid other than Val, Ile, Trp,
      Phe, or Tyr
<220> FEATURE:
<221> NAME/KEY: MISC_FEATURE
<222> LOCATION: (4)..(4)
<223> OTHER INFORMATION: X is Leu, Ile, or Phe
<220> FEATURE:
<221> NAME/KEY: MISC_FEATURE
<222> LOCATION: (5)..(5)
<223> OTHER INFORMATION: X is Phe, Leu, or Val
<220> FEATURE:
<221> NAME/KEY: MISC_FEATURE
<222> LOCATION: (6)..(6)
<223> OTHER INFORMATION: X is His, Asn, or Ser
<220> FEATURE:
<221> NAME/KEY: MISC_FEATURE
<222> LOCATION: (7)..(7)
<223> OTHER INFORMATION: X is Ala, Gly, Ser, or Thr
<220> FEATURE:
<221> NAME/KEY: MISC_FEATURE
<222> LOCATION: (8)..(8)
<223> OTHER INFORMATION: X is Gln or Met
<220> FEATURE:
<221> NAME/KEY: MISC_FEATURE
<222> LOCATION: (10)..(10)
<223> OTHER INFORMATION: X is Ile, Met, or Val
<220> FEATURE:
<221> NAME/KEY: MISC_FEATURE
<222> LOCATION: (11)..(11)
<223> OTHER INFORMATION: X is Glu, Leu, Val, Tyr, or Ile
<220> FEATURE:
<221> NAME/KEY: MISC_FEATURE
<222> LOCATION: (12)..(12)
<223> OTHER INFORMATION: X is Trp, Tyr, Val, Phe, Leu, or Ile
<220> FEATURE:
<221> NAME/KEY: MISC_FEATURE
<222> LOCATION: (13)..(13)
<223> OTHER INFORMATION: X is any amino acid other than Asp or Glu

<400> SEQUENCE: 17

Xaa Xaa Xaa Xaa Xaa Xaa Xaa Xaa Lys Xaa Xaa Xaa Xaa
1               5                   10
```